United States Patent [19]

Kishita et al.

[11] Patent Number: 5,281,695
[45] Date of Patent: Jan. 25, 1994

[54] PERFLUOROPOLYETHER COMPOUND

[75] Inventors: Hirofumi Kishita, Annaka; Yasuo Tarumi; Kouichi Yamaguchi, both of Takasaki; Takashi Matsuda, Annaka; Kouji Takano, Annaka, all of Japan

[73] Assignee: Shin-Etsu Chemical Co., Ltd., Tokyo, Japan

[21] Appl. No.: 883,195

[22] Filed: May 14, 1992

[30] Foreign Application Priority Data

May 14, 1991 [JP] Japan .................. 3-138479

[51] Int. Cl.$^5$ .............. C07C 53/50; C07C 43/11; C08G 59/00
[52] U.S. Cl. .................. 528/401; 568/615; 568/677
[58] Field of Search .............. 568/615, 677; 528/401

[56] References Cited

U.S. PATENT DOCUMENTS

| 2,713,593 | 7/1955 | Brice | 568/677 |
| 3,317,618 | 5/1967 | Haszeldine | 524/462 |
| 3,637,868 | 1/1972 | Nychka | 568/677 |
| 4,032,566 | 6/1977 | Psarras et al. | 558/447 |
| 4,647,413 | 3/1987 | Savu | 568/607 |

Primary Examiner—Frederick Krass
Attorney, Agent, or Firm—Oblon, Spivak, McClelland, Maier & Neustadt

[57] ABSTRACT

The present compound is a novel perfluoropolyether represented by the following general formula:

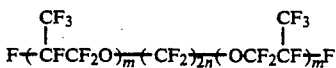

wherein m is an integer of 1 to 3 and n is an integer of 2 to 6. This compound is quite useful as an inert liquid used as a heat transfer mediums in the filed of electronic materials.

2 Claims, 1 Drawing Sheet

PERFLUOROPOLYETHER COMPOUND

BACKGROUND OF THE INVENTION

1. Field of the Invention

The present invention relates to a novel perfluoropolyether compound.

2. Description of the Prior Art

Since fluorine-containing inert liquids such as perfluoropolyether compounds are excellent in chemical stability, heat stability, and electrical insulating properties, in the field of electronic materials, they are very useful as heat transfer mediums for vapor phase reflow soldering (VPS) and as liquids used in thermal shock tests, liquid burn-in tests, and gross tests.

SUMMARY OF THE INVENTION

Therefore, an object of the present invention is to provide a novel perfluoropolyether compound quite useful for the above application.

According to the present invention, there is provided a novel perfluoropolyether compound represented by the following general formula (1):

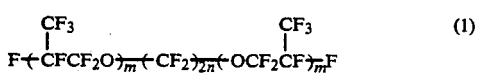
(1)

wherein m is an integer of 1 to 3 and n is an integer of 2 to 6.

The present perfluoropolyether compound is excellent in chemical stability, heat stability, and electrical insulating properties and is quite useful to be used as the above-mentioned inert liquid. Further since the present compound is a single substance, if the compound is used as an inert liquid, it is advantageous in that the range of the boiling point is quite narrow and the change in saturated vapor pressure is very small.

DETAILED DESCRIPTION OF PREFERRED EMBODIMENTS

Figure 1:
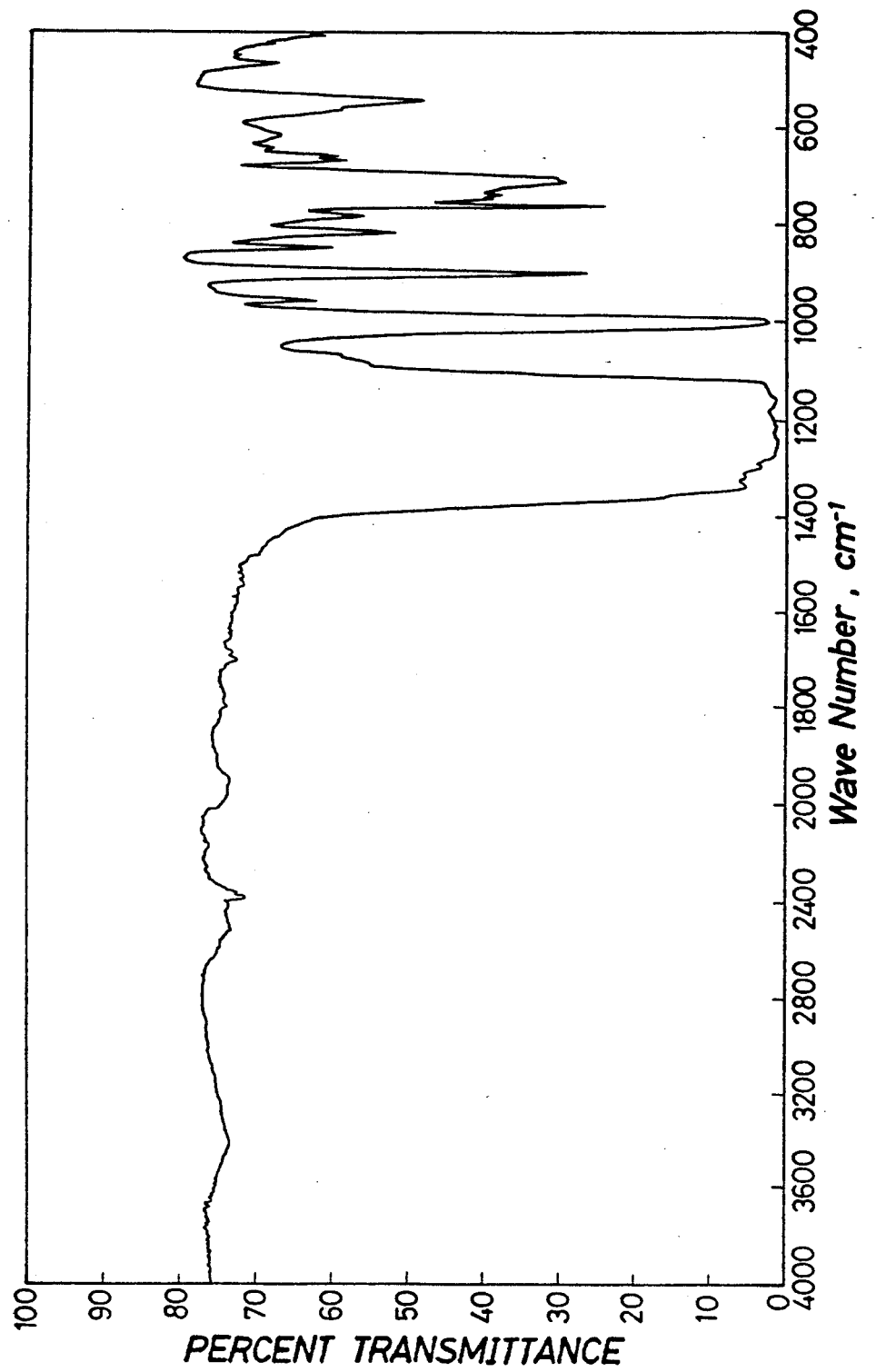
FIG. 1 is a diagram showing the IR spectrum of a perfluoropolyether compound of the present invention synthesized in Example 1.

The present perfluoropolyether compound is synthesized, for example, by reacting an iodine containing perfluoropolyether compound represented by the following general formula (2):

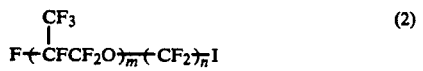
(2)

wherein m and n have the same meanings as defined above with metallic zinc in the presence of acetic anhydride. The reaction is represented by the following equation:

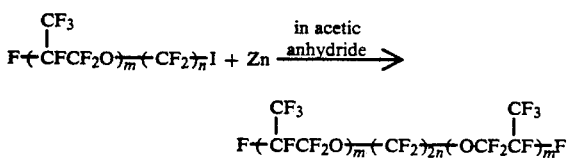

wherein m and n have the same meanings as defined above.

In this reaction, the metallic zinc acts as a condensation catalyst and the acetic anhydride acts as a co-catalyst. Generally, these metallic zinc and acetic anhydride are used in a molar ratio of the starting compound :metallic zinc:acetic anhydride in the range of 1:1:1 to 1:5:5, particularly 1:1.1:1.1 to 1:2:2. The reaction temperature is in the range of 0° to 150° C., particularly preferably 20° to 100° C.

The iodine containing perfluoropolyether compound represented by the general formula (2) which is a starting material is synthesized by methods described, for example, in Japanese Patent Publication (kokoku) 47-13011 (1972), U.S. Pat. No. 4,032,566, and J. Org. Chem. 33, 1839 (1968). Specifically, the compound can be easily synthesized, for example, by reacting an acid fluoride represented by the following general formula:

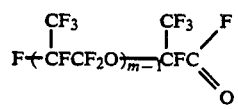

wherein m has the same meaning as defined above, a fluoride represented by the following general formula:

M—F wherein M represents one or more elements selected from
the group consisting of potassium, lead, and cesium, a perfluoroethylene, and iodine using a solvent such as diglyme and tetraglyme at a reaction temperature of about 0° to 50° C.

The thus obtained present novel perfluoropolyether compound is represented by the above general formula (1) and a typical example thereof is one wherein, in the general formula (1), n is an integer of 2 to 4.

The present compound is very useful, in the field of electronic materials, as a heat transfer medium for vapor phase reflow soldering (VPS) and as a liquid used in thermal shock tests, liquid burn-in tests, and gross tests.

EXAMPLE

EXAMPLE 1

300 g (0.52 mol) of an iodine containing perfluoropolyether compound represented by the following formula:

and 51 g (0.78 mol) of zinc powder were charged into a 1-liter 4-necked flask and 80 g (0.78 mol) of acetic anhydride was added dropwise from a dropping funnel thereto over 1 hour. After the completion of the addition, the reaction mixture was stirred for 2 hours while heating at 60° C. Thereafter, zinc compounds which were by-products and excess zinc were removed by filtration. The filtrate was washed with water to remove the acetic anhydride and the organic layer was separated. By distilling the separated organic layer, 167 g (yield: 71 %) of a fraction having a boiling point of 214° to 216° C. was obtained.

In order to identify the obtained fraction, it was subjected to elemental analysis, IR spectral analysis, and $^{19}F$NMR, which gave the results given below. From the results, it is confirmed that the obtained product is a perfluoropolyether compound represented by the following formula:

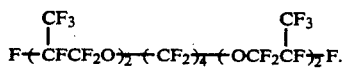

Elemental analysis

|  | C | F | O |
|---|---|---|---|
| Calculated (%) for $C_{16}F_{34}O_2$ | 21.3 | 71.6 | 7.1 |
| Found (%) | 21.1 | 71.9 | 7.0 |

$^{19}F$-NMR ($CF_3COOH$ standard)

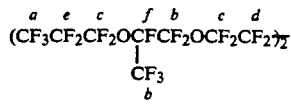

a: −3.78 ppm
b: −5.43 ppm
c: −6.67 ppm
d: −48.73 ppm
e: −52.98 ppm
f: −68.00 ppm IR spectrum The IR spectrum is shown in FIG. 1. Characteristic absorption ($cm^{-1}$) C-F: 1,000–1,400

We claim:

1. A perfluoropolyether compound represented by the following general formula (1):

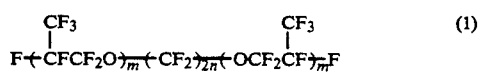

(1)

wherein m is an integer of 2 or 3 and n is an integer of 2 to 6.

2. A compound as claimed in claim 1, wherein, in said general formula (1), n is an integer of 2 to 4.

* * * * *